(12) United States Patent
Bridges et al.

(10) Patent No.: US 8,222,474 B2
(45) Date of Patent: Jul. 17, 2012

(54) FRACTIONAL EXTRACTION OF BUTADIENE

(75) Inventors: Joseph P. Bridges, Houston, TX (US); Allen David Hood, Jr., Houston, TX (US); Scott A. Smith, Clinton, IA (US); Solon B. Williams, Kingwood, TX (US)

(73) Assignee: Equistar Chemicals, L.P., Houston, TX (US)

( * ) Notice: Subject to any disclaimer, the term of this patent is extended or adjusted under 35 U.S.C. 154(b) by 450 days.

(21) Appl. No.: 12/454,778

(22) Filed: May 22, 2009

(65) Prior Publication Data

US 2010/0298621 A1  Nov. 25, 2010

(51) Int. Cl.
*C07C 7/04* (2006.01)
(52) U.S. Cl. ........ 585/810; 585/800; 585/801; 585/802; 585/803; 585/804; 585/805
(58) Field of Classification Search ........... 585/800, 585/801, 802, 803, 804, 805, 810, 833, 834, 585/836, 838, 860
See application file for complete search history.

(56) References Cited

U.S. PATENT DOCUMENTS

| | | | |
|---|---|---|---|
| 2,993,841 A | 7/1961 | Samo | |
| 3,436,436 A | 4/1969 | Takao at al. | |
| 4,054,613 A * | 10/1977 | Haskell et al. | 585/633 |
| 4,134,795 A | 1/1979 | Howatt, III | |
| 4,277,314 A | 7/1981 | Lindner et al. | |
| 7,348,466 B2 | 3/2008 | Bridges et al. | |

FOREIGN PATENT DOCUMENTS

GB  2040995 A  9/1980

OTHER PUBLICATIONS

International Bureau of WIPO, International Preliminary Report on Patentability issued Dec. 1, 2011 in International Application No. PCT/US2010/001345 filed May 6, 2010.

* cited by examiner

*Primary Examiner* — In Suk Bullock
*Assistant Examiner* — Sharon Pregler

(57) ABSTRACT

A method for the solvent extraction of 1,3-butadiene from a mixture of $C_4$ hydrocarbons that employs a distillation tower to produce the desired 1,3-butadiene product as an overhead and a separate bottoms stream that is removed from and not recycled in the solvent extraction process.

7 Claims, 1 Drawing Sheet

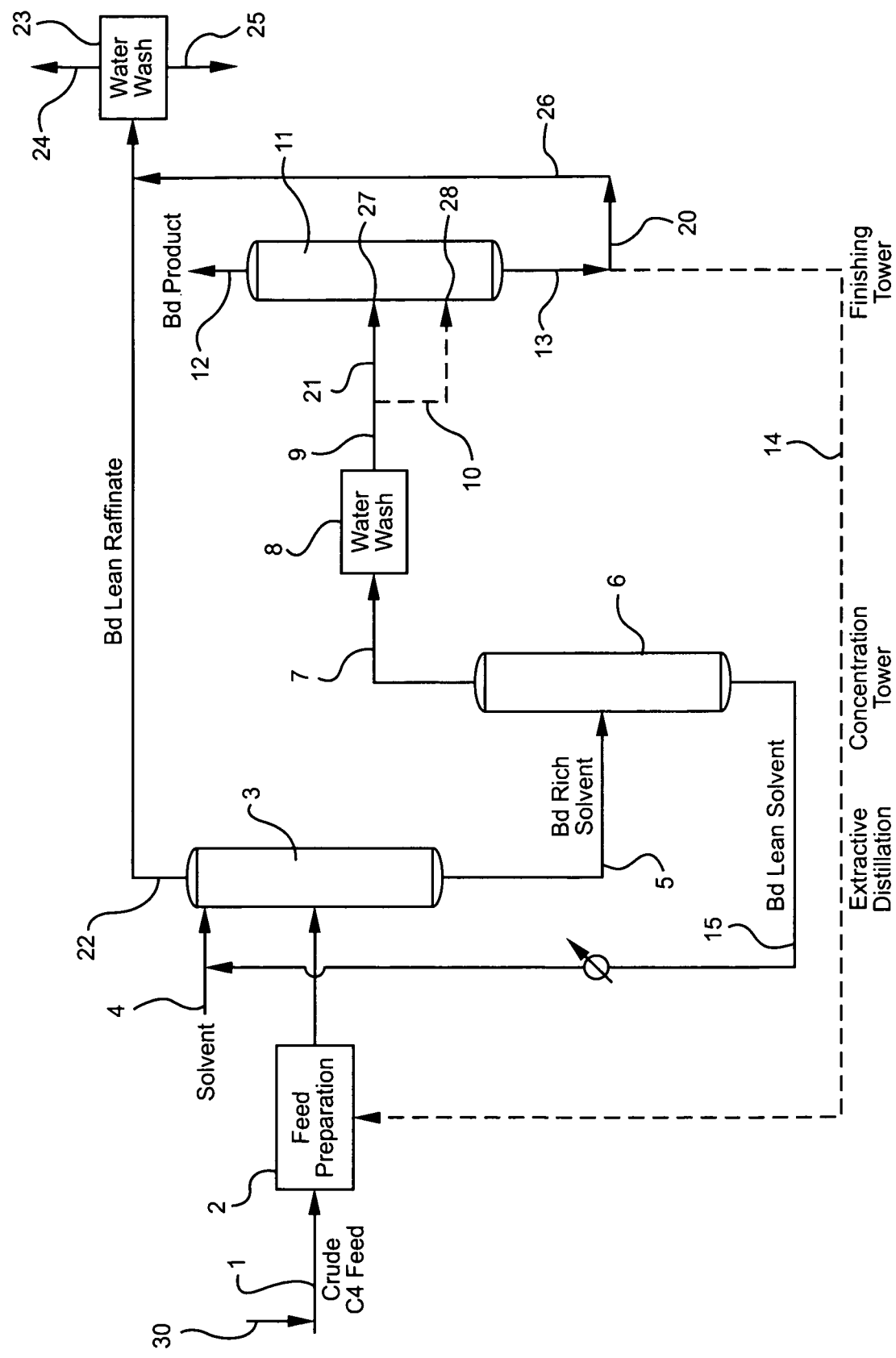

FRACTIONAL EXTRACTION OF BUTADIENE

BACKGROUND OF THE INVENTION

1. Field of the Invention

This invention relates to the fractional extraction of butadiene from a mixture of hydrocarbons having primarily four carbon atoms per molecule. More particularly, this invention relates to the fractional extraction of butadiene in a hydrocarbon thermal cracking plant.

2. Description of the Prior Art

Thermal cracking of hydrocarbons is a petrochemical process that is widely used to produce individual olefin products such as ethylene, propylene, butenes, butadiene, and aromatics such as benzene, toluene, and xylenes. In such olefin production plants, a hydrocarbonaceous feedstock such as ethane, naphtha, gas oil, or other fractions of whole crude oil or natural gas liquids is mixed with steam which serves as a diluent to keep the hydrocarbon molecules separated. This mixture, after preheating, is subjected to hydrocarbon thermal cracking at elevated temperatures of about 1,400 to 1,550° Fahrenheit (F.) in a pyrolysis furnace (steam cracker or cracker). Thermal cracking is not a catalytic process, as opposed to catalytic cracking.

The cracked product effluent from the pyrolysis furnace contains hot, gaseous hydrocarbons, both saturated and unsaturated, of great variety from 1 to 35 carbon atoms per molecule ($C_1$ to $C_{35}$). This furnace product is then subjected to further processing to produce, as products of the olefin plant, various, separate product streams of high purity, e.g., molecular hydrogen, ethylene, and propylene. After separation of these individual streams, the remaining cracked product contains essentially hydrocarbons with four carbon atoms per molecule ($C_4$'s) and heavier. This remainder is fed to a debutanizer wherein a crude $C_4$ stream is separated as overhead while a $C_5$ and heavier stream is removed as a bottoms product.

The crude $C_4$ stream has a variety of compounds such as n-butane, isobutane, 1-butene, 2-butenes (cis and trans), isobutylene, butadiene (1,2- and 1,3), vinyl acetylene, and ethyl acetylene, all of which are known to boil within a narrow range, see U.S. Pat. No. 3,436,438. Further, some of these compounds can form an azeotrope. Crude $C_4$'s are, therefore, known to be difficult to separate by simple distillation. This crude $C_4$ stream is then typically processed for the recovery, among other things, of butadiene therefrom.

The incoming crude $C_4$ stream, fresh from the cracking process, normally is subjected first to an operation designed to prepare that stream for the fractional extraction of butadiene there from. This preparation step for incoming fresh crude $C_4$ feed is used for several purposes depending on the particular processing the stream has previously undergone. For example, this preparation step can include the removal of carbonyl compounds, the removal of vinyl acetylene and ethyl acetylene, the removal of remaining $C_5$ compounds, and the like.

The thus prepared incoming crude $C_4$ stream is then subjected to fractional extraction as a first step toward separating a 1,3-butadiene product from that crude $C_4$ stream. This extraction step employs a solvent extraction process that produces a solvent extract stream that is elevated, "rich," in its 1,3-butadiene content.

The dominating process for separating 1,3-butadiene from crude $C_4$'s is known technically as "fractional extraction," but is more commonly referred to as "solvent extraction" or "extractive distillation." However it is termed, this process employs an aprotic polar compound that has a high complexing affinity toward the more polarizable butadiene than other olefins in the crude $C_4$ stream. Known solvents for this process include acetonitrile, dimethylformamide, furfural, N-methyl-2-pyrrolidone, acetone, dimethylacetamide, and the like. This process and the solvents used therein are known, see U.S. Pat. Nos. 2,993,841 and 4,134,795.

Simple thermal distillation, often called stripping, of the 1,3-butadiene rich solvent extract stream removed from the extractive distillation tower has been employed to form a 1,3-butadiene concentrate overhead stream and a separate bottoms solvent stream that is substantially reduced, "lean," in its butadiene content. The lean solvent stream from this 1,3-butadiene concentration forming tower is recycled to the extractive distillation tower for re-use to extract additional 1,3-butadiene from incoming fresh crude $C_4$ feed. The separate 1,3-butadiene concentrate stream from this concentration tower can be subjected to a water wash for the removal of traces of solvent.

Heretofore, the water washed 1,3-butadiene concentrate stream was introduced into a lower portion, the lower 25% of the vertical height, of an upstanding simple thermal distillation tower, often called a finishing tower, for the formation of the 1,3-butadiene overhead stream that is the desired product of the overall 1,3-butadiene extraction process (extractive distillation/concentration/finishing). The bottoms stream from this finishing distillation tower was typically recycled upstream of the crude $C_4$ stream preparation step aforesaid, for example, by mixing with incoming fresh crude $C_4$ feed and re-processing starting with the extractive distillation tower.

It has been surprisingly found that by carrying out the operation of the aforesaid finishing tower in a manner that produces a bottoms stream from that tower that is rich in cis-butene-2 and physically removing that bottoms stream from the overall 1,3-butadiene extraction process, additional fresh crude $C_4$ feed can be introduced into the 1,3-butadiene extraction process at a volumetric rate that is significantly greater than the volumetric rate of the removed and separated finishing tower bottoms stream.

Thus, by this invention, the capacity of the extractive distillation tower for processing incoming fresh crude $C_4$ feed is increased in an amount that is substantially greater than the amount of the finishing tower bottoms recycle stream that is redirected out of and away from the overall 1,3-butadiene extraction (production) process.

This invention, therefore, allows for the introduction into the foregoing 1,3-butadiene production process of an amount of butadiene containing fresh crude $C_4$ feed that is substantially greater than the amount of the displaced finishing tower bottoms stream, thereby substantially increasing both 1) the amount of butadiene containing crude $C_4$ material that can be fed into the 1,3-butadiene production process in general, and the extractive distillation tower in particular, and 2) the amount of 1,3-butadiene product that can be recovered from the overall 1,3-butadiene production process, all without physical modification of the extractive distillation tower, or other equipment used in the process, to increase its operating capacity.

SUMMARY OF THE INVENTION

Pursuant to this invention, by operating the aforesaid finishing tower in a manner that produces a cis-butene-2 rich bottoms stream, and physically removing that bottoms stream from the overall 1,3-butadiene extraction process, additional, fresh crude $C_4$ feed can be added to the 1,3-butadiene extraction process at a volumetric rate that is greater than the volumetric rate of the removed and separated finishing tower bottoms stream.

BRIEF DESCRIPTION OF THE DRAWING

FIG. 1 shows a prior art butadiene extraction process modified in accordance with one embodiment within this invention.

DETAILED DESCRIPTION OF THE INVENTION

FIG. 1 shows fresh crude $C_4$ feed stream 1 being fed to a feed preparation zone 2 as described above to prepare feed 1 for introduction into an extractive distillation tower 3. A solvent 4 suitable for extracting 1,3-butadiene from feed 1 is introduced into an upper portion of tower 3. A 1,3-butadiene rich solvent/$C_4$ mixture is removed via line 5 for introduction into 1,3-butadiene concentration tower 6.

In tower 6 a 1,3-butadiene concentrate overhead stream 7 is formed. In this tower a separate 1,3-butadiene lean bottoms stream 15 is removed and recycled to tower 3 for re-use in the 1,3-butadiene extraction process.

Pursuant to the prior art, stream 7 is water washed to remove solvent traces and passed via line 9 and dotted line 10 into a lower portion, point 28, of finishing distillation tower 11 to form the desired 1,3-butadiene extraction process product stream 12, and a separate bottoms stream 13. Generally, the prior art introduced stream 10 into the lower 25 percent of the finite vertical height of tower 11.

Also pursuant to the prior art, bottoms stream 13 was recycled via dotted line 14 back to zone 2 for mixing with fresh incoming feed 1 and re-extraction in tower 3.

Pursuant to this invention, finishing tower 11 is operated in a manner that deliberately produces a bottoms stream 13 that is rich in cis-butene-2, and none of that cis-butene-2 rich stream 13 is recycled to zone 2, but rather is instead removed from the overall 1,3-butadiene extraction process by way of line 20.

Although there are a number of ways tower 11 can be operated to produce a bottoms stream 13 that is rich in cis-butene-2, all of which will be obvious to one skilled in the art once this invention has been disclosed to them, this invention will, for sake of clarity and brevity, hereafter be described in detail in respect of the point of introduction of stream 9 into tower 11.

Pursuant to the point-of-introduction embodiment of this invention, stream 9, instead of being introduced into a lower portion of tower 11 as was done with stream 10, is introduced into a central portion, e.g., point 27, of the finite vertical height of tower 11 which will produce a bottoms stream 13 that is rich in cis-butene-2. The cis-butene-2 rich bottoms stream 13 is then diverted out of and away from the overall 1,3-butadiene extraction process by way of line 20.

For the purposes of this invention, stream 21 can be introduced at a point 27 that is at a level above (starting from the lowest point where bottoms stream 13 is withdrawn from tower 11) about 40% of the finite vertical height of tower 11. Preferably stream 21 is introduced at a point 27 and is at a level that is in the range of from about 40% to about 60% of the vertical height of tower 11.

One way to dispose of stream 20 away from the 1,3-butadiene extraction process of this invention is to, via line 26, combine it with the 1,3-butadiene lean raffinate overhead stream 22 that is recovered from tower 3. The combined streams 20 and 22 can then be water washed at 23 for the removal of traces of solvent in line 25 and the production of $C_4$ raffinate stream 24.

If stream 26, by way of the operation of tower 11, does not chemically resemble stream 22, then stream 26 can be disposed of in other ways in the plant or elsewhere that will be obvious to one skilled in the art.

By whatever way stream 20 is disposed of outside of the overall 1,3-butadiene extraction process comprised of units 3,6, and 11 of FIG. 1, pursuant to the surprising results of this invention, additional fresh crude $C_4$ feed 30 can be added to the flow of original feed 1 in an amount that exceeds the amount of stream 20 that is removed from that overall 1,3-butadiene extraction process.

Generally, when tower 11 is operated pursuant to this invention, the addition of fresh crude $C_4$ feed 30 to feed 2 to replace the diverted stream 20 can be at a volumetric rate that is at least about 1.1 times the volumetric rate of that diverted stream 20. More particularly, it has been found that, depending on the particular feed composition, operating conditions, and the like, additional fresh crude $C_4$ feed 30 can be added to original feed 2 at a volumetric rate that is from about 1.1 to about 2 times the volumetric rate of removed stream 20.

The cis-butene-2 content of stream 20 can vary widely, again depending on the chemical make-up of feed 2, the specific processing details of the particular 1,3-butadiene extraction process employed, and the like. However, pursuant to this invention, so long as tower 11 is operated so that additional fresh crude $C_4$ feed 30 can be added to original feed 2 at a volumetric rate that is at least 1.1 times the volumetric rate of diverted stream 20, the beneficial results of this invention will be achieved. To realize the benefits of this invention, tower 11 can generally be operated in a manner such that stream 20, as it is removed from the overall 1,3-butadiene extraction process, contains at least about 70 wt. % cis-butene-2 based on the total weight of that stream 20.

EXAMPLE

A feed stream 1 having a composition of about 35% 1,3-butadiene, less than about 1% 1,2-butadiene, about 5% cis-butene-2, and about 7% trans-butene-2, with the remainder being made up of a combination of butene-1, isobutylene, and saturates was employed in the process of FIG. 1 at an incoming flow rate to zone 2 of about 745 gallons per minute (gpm). All % were wt. % based on the total weight of the stream. Unless expressly stated otherwise, all % given in this Example are wt. % based on the total weight of the stream in question.

This foregoing original feed was employed in the process of FIG. 1 in both the aforesaid prior art mode (recycling stream 14), and pursuant to this invention (removal of stream 20). This feed was, in both cases, at a temperature of about 105 F and pressure of about 100 pounds per square inch gauge (psig).

Tower 3 was operated using a conventional mixture of acetonitrile in major amount and water in minor amount as the extractive solvent, a bottoms temperature of about 245 F and pressure of about 80 psig, and an overhead temperature of about 115 F and pressure of about 65 psig with an external reflux flow rate of about 860 gpm and a solvent flow rate of about 2,850 gpm.

Tower 6 was operated at a bottoms temperature of about 280 F at about 70 psig, and an overhead temperature of about 125 F at about 65 psig with an external reflux flow rate of about 515 gpm.

Tower 11 was operated at a bottoms temperature of about 175 F at about 130 psig, and an overhead temperature of about 130 F at about 80 psig with an external reflux flow rate of about 2,160 gpm.

When tower 11 was operated pursuant to the prior art recycle mode, stream 10 was introduced into tower 11 at a level in the lower 25% of the vertical height of tower 11.

When tower 11 was operated pursuant to this invention, stream 21 was introduced into tower 11 at a level of about 50% of the vertical height of tower 11

When bottoms stream 13 of tower 11 was recycled by way of line 14 to zone 2 in the prior art manner, stream 14 contained about 37% 1,3-butadiene, about 9% 1,2-butadiene, about 44% cis-butene-2, and about 9% trans-butene-2 with the remainder being made up of a combination of butene-1, isobutylene, and saturates.

Stream 14 was recycled to zone 2 at the rate of 40 gpm.

When bottoms stream 13 of tower 11 was removed by way of stream 20, i.e., removed from the overall 1,3-butadiene extraction process pursuant to this invention, stream 20 contained about 1.5% 1,3-butadiene, about 16% 1,2-butadiene, about 75% cis-butene-2, and about 5% trans-butene-2 with the remainder being made up of a combination of butene-1, isobutylene, and saturates.

Stream 20 was removed from the overall 1,3-butadiene extraction process at the flow rate of about 40 gpm.

When operating pursuant to this invention, the volumetric amount of additional fresh feed 30 that could be added to original feed 1 for processing in tower 3 was about 55 gpm. Thus, the volumetric amount of additional feed 30 that could be added to feed 1 was substantially greater than the about 30 gpm volumetric amount of stream 20 that was removed from the overall 1,3-butadiene extraction process.

When operating in the prior art mode, product stream 12 contained about 99.6% 1,3-butadiene, and less than about 0.4% of butene-1, cis-butene-2, and trans-butene-2 combined. The flow rate for this stream was about 240 gpm.

When operating pursuant to this invention, product stream 12 had essentially the same composition as prior art stream 12 aforesaid, but its flow rate had increased to about 260 gpm.

When operating pursuant to this invention, the chemical composition of stream 20 was sufficiently compatible with the chemical composition of raffinate stream 22 that these two streams could be combined and processed together in tower 23.

We claim:

1. In a method for processing at least one first crude C4 feed mixture containing at least 1,3-butadiene and cis-butene-2 to produce a 1,3-butadiene process product, said method comprising extractive distillation in a first tower, said first crude C4 feed mixture being extractively distilled in said first tower with a solvent to produce a solvent 1,3-butadiene mixture that is rich in 1,3-butadiene and contains cis-butene-2, thermally distilling in a second tower said solvent 1,3-butadiene mixture containing cis-butene-2 to separate said solvent and produce a 1,3-butadiene concentrate containing cis-butene-2, thermally distilling in a third tower said 1,3-butadiene concentrate containing cis-butene-2 to form a 1,3-butadiene product as an overhead stream and a separate C4 bottoms stream containing cis-butene-2, said third tower having a finite vertical height, the improvement comprising carrying out said thermal distillation of said 1,3-butadiene concentrate containing cis-butene-2 in said third tower in a manner that produces a cisbutene-2 bottoms stream that is rich in cis-butene-2 and comprises less than 20 wt % butadiene, physically removing said cisbutene-2 rich bottoms stream from said process at a first volumetric rate, and replacing said removed cis-butene-2 rich bottoms stream with fresh crude C4 feed to said first tower that is in addition to said first crude C4 feed, said addition of said fresh crude C4 feed being at a second volumetric rate that is at least about 1.1 times said first volumetric rate of said removed cis-butene-2 rich bottoms stream.

2. The method of claim 1 wherein said additional fresh crude C4 feed is added at a second volumetric rate that is from about 1.1 to about 2 times said first volumetric rate of removed cis-butene-2 rich bottoms stream.

3. The method of claim 1 wherein said removed cis-butene-2 rich bottoms stream contains at least about 70 wt. % cis-butene-2 based on the total weight of that bottoms stream.

4. The method of claim 1 wherein said 1,3-butadiene concentrate containing cisbutene-2 stream is introduced into a central portion of said vertical height of said third tower.

5. The method of claim 4 wherein said 1,3-butadiene concentrate containing cisbutene-2 stream is introduced into said third tower at a level above about 40% of said vertical height of said third tower.

6. The method of claim 4 wherein said 1,3-butadiene concentrate containing cisbutene-2 stream is introduced into said third tower at a level in the range of from about 40% to about 60% of said vertical height of said third tower.

7. The method of claim 1 wherein said removed cis-butene-2 rich bottoms stream is mixed with a butadiene lean raffinate stream.

* * * * *